(12) United States Patent
Bierman (10) Patent No.: US 7,520,870 B2
(45) Date of Patent: Apr. 21, 2009

(54) ANCHORING SYSTEM FOR A MEDICAL ARTICLE

(75) Inventor: Steven F. Bierman, Del Mar, CA (US)

(73) Assignee: Venetec International, Inc., Covington, GA (US)

( * ) Notice: Subject to any disclaimer, the term of this patent is extended or adjusted under 35 U.S.C. 154(b) by 307 days.

(21) Appl. No.: 11/266,683

(22) Filed: Nov. 3, 2005

(65) Prior Publication Data

US 2006/0064063 A1 Mar. 23, 2006
US 2007/0129685 A2 Jun. 7, 2007

Related U.S. Application Data

(63) Continuation of application No. 10/316,212, filed on Dec. 10, 2002, now Pat. No. 6,979,320, which is a continuation of application No. 09/375,744, filed on Aug. 17, 1999, now Pat. No. 6,491,664.

(60) Provisional application No. 60/228,797, filed on Aug. 18, 1998.

(51) Int. Cl.
*A61M 5/32* (2006.01)
(52) U.S. Cl. .................................. 604/180; 604/174
(58) Field of Classification Search ................. 604/116, 604/174–180; 128/DIG. 26; 24/462, 545, 24/555; 248/74.2
See application file for complete search history.

(56) References Cited

U.S. PATENT DOCUMENTS

| | | | |
|---|---|---|---|
| 2,525,398 A | 10/1950 | Collins | |
| 2,533,961 A | 12/1950 | Rousseau et al. | |
| 2,707,953 A | 5/1955 | Ryan | |
| 3,059,645 A | 10/1962 | Hasbrouck et al. | |
| 3,064,648 A | 11/1962 | Bujan | |
| 3,167,072 A | 1/1965 | Stone et al. | |
| 3,568,679 A | 3/1971 | Reif | |
| 3,574,306 A | 4/1971 | Alden | |
| 3,602,227 A | 8/1971 | Andrew | |
| 3,677,250 A | 7/1972 | Thomas | |
| 3,766,915 A | 10/1973 | Rychlik | |
| 3,856,020 A | 12/1974 | Kovac | |
| 3,900,026 A | 8/1975 | Wagner | |
| 3,906,946 A | 9/1975 | Nordström | |

(Continued)

FOREIGN PATENT DOCUMENTS

DE 2341 297 A1 8/1973

(Continued)

*Primary Examiner*—Nicholas D Lucchesi
*Assistant Examiner*—Victoria P Campbell
(74) *Attorney, Agent, or Firm*—Knobbe Martens Olson & Bear LLP (57) ABSTRACT

An anchoring system includes a simply-structured device which permits a portion of a catheter or similar medical article to be easily anchored to a patient, desirably without the use of tape or needles and suturing. The anchoring system desirably includes a retainer and an anchor pad. The retainer is sized and configured to accept and retain a section of a catheter within the anchoring system and desirably includes a pair of posts and a clip. The posts are sized and configured to releasably accept holes formed in the catheter or catheter fitting. The clip is sized and configured to releasably accept a portion of the catheter. The anchor pad secures the retainer to a patient's skin.

19 Claims, 7 Drawing Sheets

U.S. PATENT DOCUMENTS

| | | | |
|---|---|---|---|
| 3,920,001 A | 11/1975 | Edwards | |
| 3,942,228 A | 3/1976 | Buckman et al. | |
| 3,973,565 A | 8/1976 | Steer | |
| 4,020,835 A | 5/1977 | Nordstrom et al. | |
| 4,025,015 A * | 5/1977 | Kolic | 248/205.3 |
| 4,059,105 A | 11/1977 | Cutruzzula et al. | |
| 4,082,094 A | 4/1978 | Dailey | |
| 4,116,196 A | 9/1978 | Kaplan et al. | |
| 4,129,128 A | 12/1978 | McFarlane | |
| 4,161,177 A | 7/1979 | Fuchs | |
| 4,250,880 A | 2/1981 | Gordon | |
| 4,316,461 A | 2/1982 | Marais et al. | |
| 4,326,519 A | 4/1982 | D'Alo et al. | |
| 4,397,647 A | 8/1983 | Gordon | |
| 4,405,163 A | 9/1983 | Voges et al. | |
| 4,453,933 A | 6/1984 | Speaker | |
| 4,480,639 A | 11/1984 | Peterson et al. | |
| 4,633,863 A | 1/1987 | Filips et al. | |
| 4,660,555 A | 4/1987 | Payton | |
| 4,711,636 A | 12/1987 | Bierman | |
| 4,742,824 A | 5/1988 | Payton et al. | |
| 4,752,292 A | 6/1988 | Lopez et al. | |
| 4,795,429 A | 1/1989 | Feldstein | |
| 4,826,486 A | 5/1989 | Palsrok et al. | |
| D301,684 S * | 6/1989 | Herzog | D8/356 |
| 4,852,844 A | 8/1989 | Villaveces | |
| 4,857,058 A | 8/1989 | Payton | |
| 4,880,412 A | 11/1989 | Weiss | |
| 4,897,082 A | 1/1990 | Erskine | |
| 4,898,587 A | 2/1990 | Mera | |
| 4,919,654 A | 4/1990 | Kalt | |
| 4,955,864 A | 9/1990 | Hajduch | |
| 4,997,421 A | 3/1991 | Palsrok et al. | |
| 5,084,026 A | 1/1992 | Shapiro | |
| 5,090,645 A * | 2/1992 | Zuercher | 248/68.1 |
| 5,137,519 A | 8/1992 | Littrell et al. | |
| 5,192,273 A | 3/1993 | Bierman et al. | |
| 5,192,274 A | 3/1993 | Bierman | |
| 5,209,441 A * | 5/1993 | Satoh | 248/74.2 |
| 5,354,282 A | 10/1994 | Bierman | |
| 5,382,239 A | 1/1995 | Orr et al. | |
| 5,413,562 A | 5/1995 | Swauger | |
| 5,415,287 A * | 5/1995 | Hamano et al. | 206/363 |
| 5,456,671 A | 10/1995 | Bierman | |
| 5,470,321 A | 11/1995 | Forster et al. | |
| 5,484,425 A | 1/1996 | Fischell et al. | |
| 5,496,282 A | 3/1996 | Militzer et al. | |
| 5,496,283 A | 3/1996 | Alexander | |
| 5,578,013 A * | 11/1996 | Bierman | 604/180 |
| 5,693,032 A | 12/1997 | Bierman | |
| 5,702,369 A | 12/1997 | Mercereau | |
| D389,911 S | 1/1998 | Bierman | |
| 5,722,959 A | 3/1998 | Bierman | |
| 5,810,781 A | 9/1998 | Bierman | |
| D399,954 S | 10/1998 | Bierman | |
| 6,032,433 A * | 3/2000 | Hatziathanasiou | 52/742.12 |
| 6,213,979 B1 | 4/2001 | Bierman | |
| 6,224,571 B1 * | 5/2001 | Bierman | 604/174 |
| 6,491,664 B2 | 12/2002 | Bierman | |

FOREIGN PATENT DOCUMENTS

| | | |
|---|---|---|
| EP | 0 169 704 | 1/1986 |
| EP | 0 690 704 A1 | 1/1986 |
| EP | 0 247 590 A2 | 12/1987 |
| GB | 2 063 679 A | 6/1981 |
| GB | 2 086 466 A | 5/1982 |
| JP | 1980-501090 | 12/1980 |
| JP | 1995-500976 | 2/1995 |
| WO | WO 80/01458 | 7/1980 |
| WO | WO 92/19309 | 11/1992 |
| WO | WO 98/53872 | 12/1998 |

* cited by examiner

ANCHORING SYSTEM FOR A MEDICAL ARTICLE

RELATED CASES

This application is a continuation of application Ser. No. 10/316,212, filed on Dec. 10, 2002, now issued as U.S. Pat. No. 6,979,320 on Dec. 27, 2005, which is a continuation of application Ser. No. 09/375,744, filed on Aug. 17, 1999, now issued as U.S. Pat. No. 6,491,664 on Dec. 10, 2002, which claims the benefit of U.S. Provisional Application No. 60/228,797, filed on Aug. 18, 1998, each of which is hereby incorporated by reference in its entirety.

BACKGROUND OF THE INVENTION

1. Field on the Invention

The present invention relates in general to an anchoring system for securing a medical article to a patient and, in particular, to an anchoring system for securing a catheter or other elongated medical article to a patient to inhibit movement or migration of the catheter or medical article relative to the patient.

2. Description of Related Art

It is very common in the treatment of patients to utilize catheters to introduce fluids and medications directly into the patient or to withdraw fluids from the patient. For example, one catheter utilized to introduce fluids into a patient is a midline catheter.

In many cases, the catheter remains in place for several days or weeks. In order to secure the catheter in position at the insertion site, a health care provider often secures the catheter to the patient using tape. That is, the health care provider commonly places long pieces of tape across a section of the catheter near the insertion site in a crisscross pattern to secure the catheter to the patient's skin. This securement inhibits movement of the catheter relative to the insertion site, as well as prevents the catheter from snagging on the bed rail or other objects.

Tape, however, often collects dirt and other contaminates. Normal protocol therefore requires periodic (e.g., daily) tape changes to inhibit bacteria and germ growth at the securement site. Frequent tape changes, however, create the problem of excoriation of the patient's skin. Additionally, valuable time is spent applying and reapplying the tape. Further, because many health care providers find the taping procedure difficult and cumbersome when wearing latex gloves, they often remove their gloves when taping. Not only does this further lengthen the taping procedure, but it also subjects the health care provider to possible infection. Moreover, even if health care providers remain gloved, contact between the adhesive surface of the tape and the latex gloves causes micro-holes in the gloves, which subjects the health care provider to possible infection.

As an alternative to tape securement, some catheters include an integrated or a movable flexible clamp with winged extensions. These extensions are sutured to the patient's skin in order to secure the catheter in position at the insertion site. In other applications, the flexible claim is covered by a rigid box clamp, which receives the catheter/clamp combination in a friction-fit manner. The rigid box clamp and the flexible clamp have lateral, aligned holes in them, which allow the combination to be sutured to the patient's skin. Although this technique securely attaches the catheter to the patient, it obviously is painful and uncomfortable for the patient. This prior retention procedure is also time consuming and inconvenient, poses the risk of needle-stick to the health care provider, and risks suture-site infection to the patient.

In addition, suture material tends to exhibit poor gripping on medical tubes and can cut through the winged extension of the flexible clamp, if a rigid clamp is not used. The use of a rigid clamp, however, complicates the securement procedure by adding yet another component that can be dropped on the floor and become unsterile. In addition, the sutured securement of the flexible clamp or the flexible/rigid clamp assembly, does not permit easy release of the catheter from the patient for dressing changes and insertion site cleansing.

SUMMARY OF THE INVENTION

An aspect of the present invention involves a simply-structured anchoring system that secures an elongated medical article (e.g., a catheter) in a fixed position relative to an insertion site and resists tugs on the medical article, while facilitating intentional release of the medical article from the anchoring system for dressing changes or other servicing. Tools, such as hemostats or surgical clamp, need not be used to release the medical article from the anchoring system.

In one mode, the anchoring system comprises an anchoring pad having a first surface and a second surface. The second surface includes an adhesive layer that covers at least a portion of the second surface. A retainer is mounted on the first surface of the anchor pad for receiving a portion of the medical article. The retainer includes a base that is attached to the first surface and at least one post that extends from the base. The post has a securing portion, which is arranged toward an outer end of the post. At least one clip is also formed on the retainer. The clip is sized and configured to engage at least a portion of the medical article.

Another aspect of the present invention involves an anchoring system for securing an elongated medical article to a patient. The medical article includes at least one aperture. The anchoring system comprises an anchor pad and a retainer mounted to the anchor pad. The retainer includes a first retention member that is positioned generally upright relative to the anchor pad. The first retention member is configured to be inserted through the corresponding aperture of the medical article. The retainer also includes a second retention member that is coupled to an anchor pad. At least a portion of the second retention member is positioned to lie generally normal to the first retention member, and is spaced from the anchor pad by a distance so dimensioned to permit at least a section of the elongated medical article to be placed between the portion of the second retention member and the anchor pad.

In accordance with another aspect of the present invention, a method of securing a medical article to the body of a patient, wherein the medical article includes an elongated body with pliable wings that extend out from the body, with each wing including at least one suture hole, is provided. The method involves providing a retainer that has at least first and second posts, which are spaced apart. A clip of the retainer is positioned to the side of the post. The first post is inserted into one of the suture holes of the pliable wings of the medical article. The pliable wings are stretched so as to position that other suture hole over to the second post. The stretched wing is then hooked over the second post so as to insert the second post into the corresponding suture hole. A section of the elongated body is inserted into the clip and positioned therein so as to inhibit the elongated body from disengaging from the clip. In the preferred mode, the retainer is adhered to the body of the patient.

Further aspects, features and advantages of the present invention will become apparent from the detailed description of the preferred embodiment that follows.

BRIEF DESCRIPTION OF THE DRAWINGS

The above mentioned and other features of the invention will now be described with reference to the drawings of preferred embodiments of the present anchoring system. The illustrated embodiments of the anchoring system are intended to illustrate, but not to limit the invention. The drawings contain the following figures:

FIG. 3a is a front elevation view of the retainer of FIG. 2a;

FIG. 4a is a side elevation view of the retainer of FIG. 3a;

DETAILED DESCRIPTION OF PREFERRED EMBODIMENTS OF THE INVENTION

The present embodiment of the anchoring system for a medical article is disclosed in the context of an exemplary midline catheter. The principles of the present invention, however, are not limited to midline catheters. Instead, it will be understood by one of skill in this art, in light of the present disclosure, that the anchoring system and retainer disclosed herein also can be successfully utilized in connection with other types of medical articles, including other types of catheters, fluid drainage and delivery tubes and electrical wires. For example, but without limitation, the retainer disclosed herein can also be configured to receive and secure central venous catheters, peripheral catheters, peripherally inserted central catheters, hemodialysis catheters, surgical drainage tubes, feeding tubes, chest tubes, nasogastric tubes, scopes, as well as electrical wires or cables connected to external or implanted electronic devices or sensors, provided that these device include either an integrated or movable fitting (e.g., a winged fitting) with one or more securement apertures. One skilled in the art may also find additional applications for the devices and systems disclosed herein. Thus, the illustration and description of the anchoring system in connection with a midline catheter is merely exemplary of one possible application of the anchoring system. The catheter in the illustrated embodiment includes at least a pliable or deformable winged fitting, being formed of silicone or latex. An exemplary midline catheter, in which both the catheter body and the winged fitting are formed of silicone, is available commercially from Becton, Dickinson and Company of Sandy, Utah.

Each of the embodiments described herein employ some basic concepts characteristic of the anchoring system, namely releasable engagement of the medical article to a patient. The releasable engagement is achieved by cooperation among post, clip and catheter fitting elements. This cooperation allows the catheter to be disconnected from the anchoring system, and from the patient, for any of a variety of known purposes. For instance, the health care provider may want to remove the catheter from the anchoring system to ease disconnection of the catheter from the insertion point or to clean the patient. The disengagement of the catheter from the anchoring system, however, can be accomplished without removing the anchoring system from the patient. In addition, the disengagement can be accomplished without destroying the anchoring system and without the use of tools, such as, for example, a hemostat or surgical clamp.

Each of the embodiments described herein also inhibit axial and rotational movement of the catheter with respect to the anchoring system. Axial movement is generally inhibited by the holding effect provided by the posts, which cooperate with holes in the winged catheter fitting. Rotational movement is generally inhibited by the holding effect provided by the clip, which cooperates with the post to resist movement of the catheter which could otherwise cause the catheter fitting to rock, roll, slip or slide from engagement with the posts.

To assist in the description of these components of the anchoring system 10, the following coordinate terms are used. A "longitudinal axis" is generally parallel to the section of the catheter 12 retained by the anchoring system 10. A "lateral axis" is normal to the longitudinal axis and is generally parallel to the plane of the anchor pad 56. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. Also, the terms "proximal" and "distal", which are used to describe the present anchoring system 10, are used consistently with the description of the exemplary application. Thus, proximal and distal are used in reference to the center of the patient's body. A detailed description of the anchoring system 10, and its associated method of use, now follows.

Figure 1:
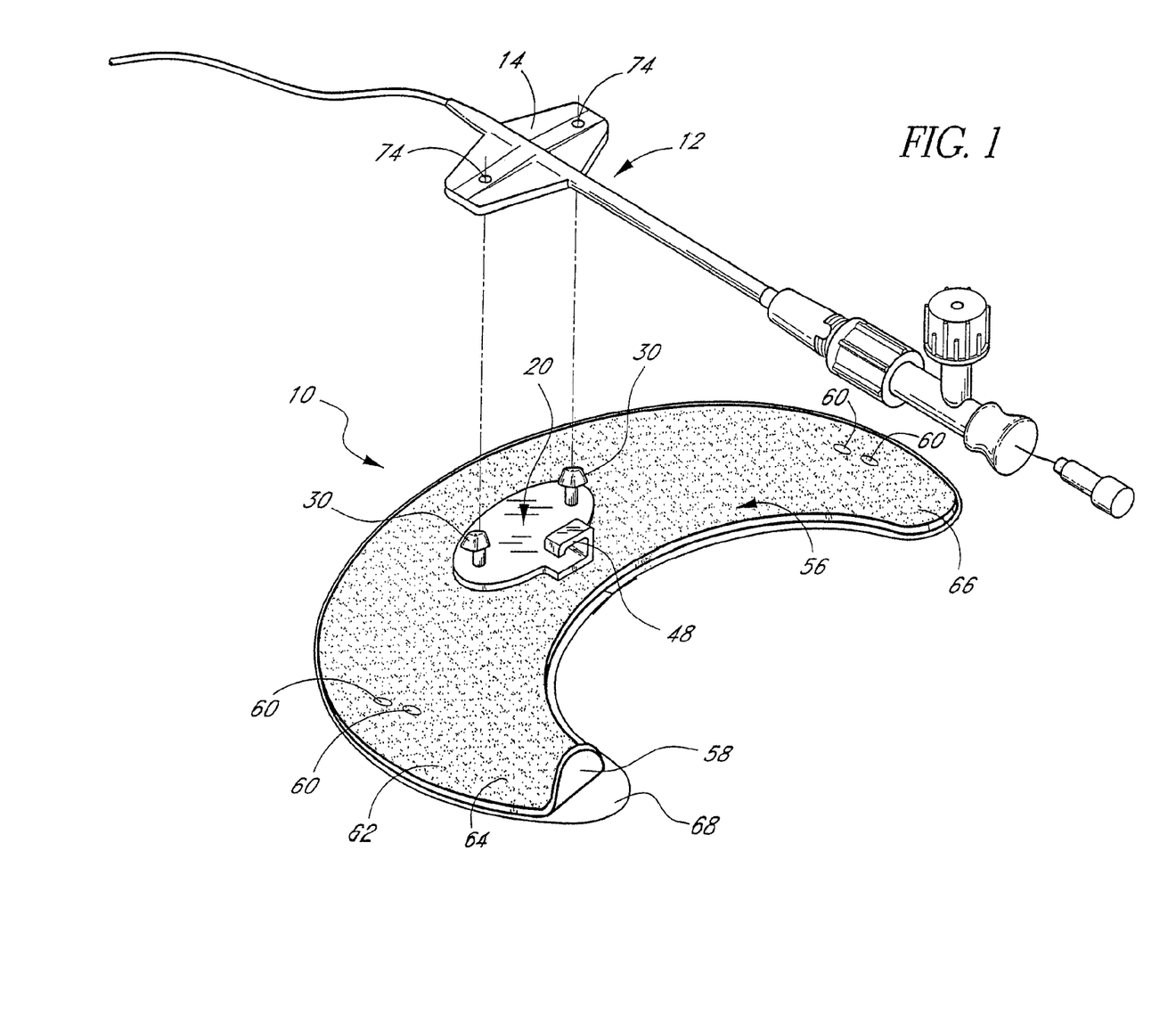
FIG. 1 is a perspective view of an anchoring system in accordance with a preferred embodiment of the present invention and illustrates an exemplary catheter positioned above the anchoring system.
Figure 2A:
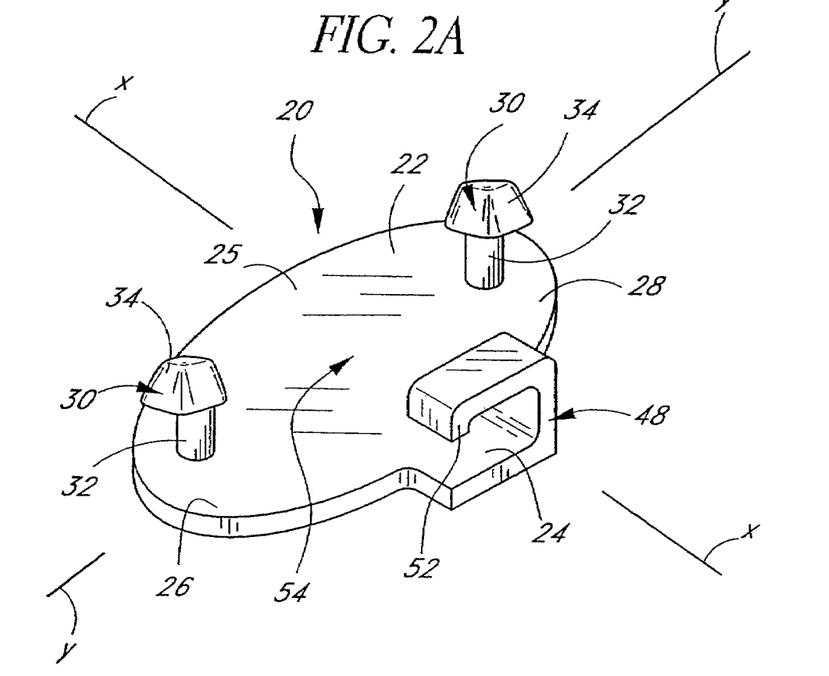
FIG. 2a is a perspective view of a retainer of the anchoring system of FIG. 1.
Figure 2B:
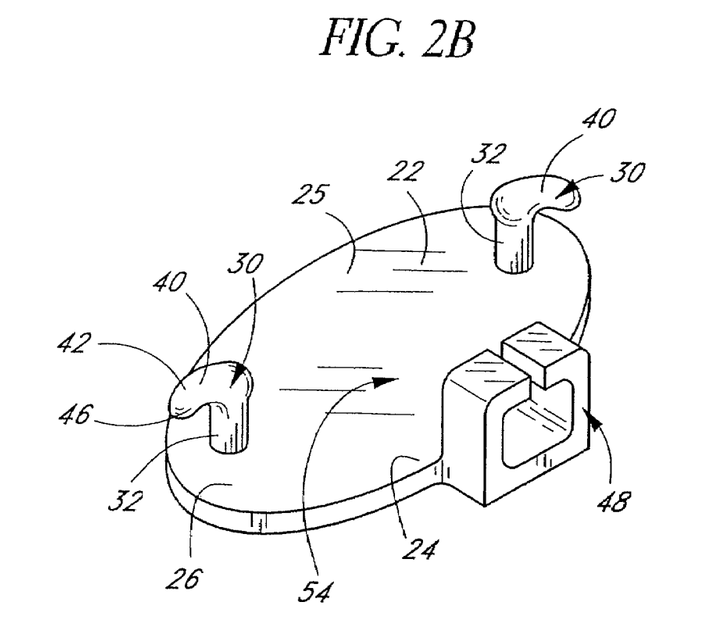
FIG. 2b is a perspective view of another embodiment of a retainer that can be used with an anchoring system similar to that of FIG. 1.

With reference now to FIGS. 1 and 2, an anchoring system 10 is illustrated and constructed in accordance with preferred embodiments of the present invention. The system comprises a retainer 20 and an anchor pad 56. The anchor pad 56 secures the retainer 20 to a patient's skin. The anchor pad 56 has a lower adhesive surface 58 which adheres to the skin of a patient and an upper surface 62 which supports and secures the retainer 20.

The retainer 20 is sized and configured to accept and retain a section of a catheter 12 (FIGS. 6-8) within the anchoring system 10. The retainer desirably includes at least first and second retention members. The first retention member is positioned generally upright relative to the anchor pad 56, and is configured to inserted through the corresponding aperture 74 (e.g., suture hole) of the catheter fitting 14. The first retention member is configured to engage a portion of the catheter fitting 14 about the aperture 74 so as to inhibit unintentional disengagement of the catheter 12 from the first retention member. The second retention member is coupled to the anchor pad 56. At least a portion of the second retention member is positioned to lie generally normal to the first retention member and is spaced from the anchor pad 56 by a sufficient distance to permit at least a section of the catheter 12 to be placed between the portion of the second retention member and the anchor pad 56. The second retention member also is configured to inhibit the received section of the catheter 12 from pulling out of engagement with the second retention member.

In the illustrated embodiment, the first retention member desirably comprises a post 30 and the second retention member desirably comprises a clip 48. More preferably, the retainer 20 includes a pair of posts 30 and a clip 48, which is positioned to the side of the posts 30; however, the retainer 20 can include any combination of posts and clips in order to suit a particular application, as those skilled in the art will appreciate. For instance, the retainer 20 can include a single post 30 positioned between a pair of clips 48 on the retainer. The posts 30 are sized and configured to releasably accept holes 74 formed in the catheter 12 or a winged catheter fitting 14. The clip 48 is sized and configured to releasably accept a portion of the catheter 12.

With reference to FIG. 2a, the retainer 20 includes a rigid structure principally formed by a base 22. In the illustrated embodiment, the base 22 is integrally formed with the posts 30 and the clip 48 to comprise a unitary retainer 20. This can be accomplished in any of a variety of ways well known to those skilled in the art. For instance, the entire retainer 20 can be injection molded in order to reduce fabrication costs.

Additionally, as will be apparent from the below description, several features of the retainer 20 (e.g., a clip, and to some extent the post(s) and the retainer itself) desirably are flexible. Suitable rigid but flexible materials include, for example, but without limitation, plastics, polymers or composites such as polypropylene, polyethylene, polycarbonate, polyvinylchloride, acrylonitrile butadiene styrene, nylon, olefin, acrylic, polyester, as well as moldable silicon, thermoplastic urethane, thermoplastic elastomers, thermoset plastics and the like. The illustrated retainer 20 preferably is formed by injection molding using a plastic or polymer material. However, other materials can be utilized, and the retainer 20 can comprise a non-unitary base, posts and/or clip.

As seen in FIG. 2a, the base 22 comprises an elongated body formed substantially along a plane in the longitudinal (X-X) and lateral (Y-Y) directions. The base 22 has a distal end 24 and a proximal end 25. The base 22 can be configured in a wide variety of shapes, such as square, circular, triangular, curvilinear or the like in order to suit a particular application. For example, the base 22 may be configured similar to the shape of the anchor pad 56. The illustrated embodiment shows a generally oval base including first and second lateral sides 26, 28.

The longitudinal dimension of the base 22 desirably is sufficiently long to provide stability to the catheter 12 along its length. That is, the longitudinal length of the retained catheter 12 portion is sufficient to inhibit rocking of the catheter 12 relative to the retainer 20 (i.e., to prevent the retainer 20 from acting as a fulcrum for the catheter 12). This desirably is also true for the lateral dimension of the retainer 20. In addition, the lateral dimension of the base 22 desirably allows the health care provider to easily and naturally grip the retainer 20, as well as provides space on which to locate one or more posts and one or more clips.

Figure 3A:
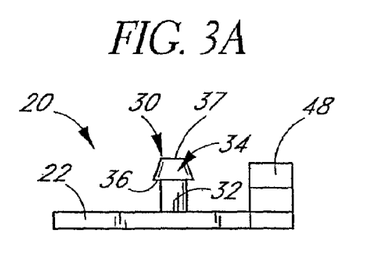
Figure 4A:
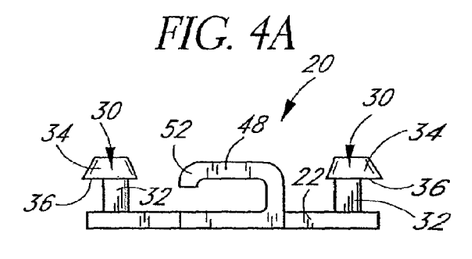

With reference now to FIGS. 2a, 3a and 4a, one or more posts 30 extend from the base 22. The illustrated embodiment includes two posts 30 that extend substantially upright relative to the base 22. However, the base 22 can also include additional posts 30 to suit a specific application. For example, where the retainer 20 is designated to secure a relatively large catheter 12 or catheter fitting 14, the base 22 can include four posts arranged at the corners of a rectangle, for greater stability. Also, three posts can be used to firmly anchor a Y-site fitting.

Each post 20 includes a shank or shaft 32, attached to and extending from the base 22. The shaft 32 can have a variety of lengths and a variety of distances between them, depending upon the particular application and the particular fitting 14 with which they are to interact to mount the catheter 12. For anchoring catheters and medical tubing, each shaft 32 desirably has a length of about 2 mm to 20 mm, and more particularly a length of about 4 mm; however, longer or shorter lengths also are possible. The shafts 32 are laterally spaced at least wide enough to accommodate the catheter to be anchored, and in the illustrated embodiments, the shafts 32 are spaced to accommodate the fitting 14 which secures the catheter 12. Desirably, the shafts 32 are spaced apart by a distance slightly greater than the distance between the corresponding suture holes 74 on the retainer 20. In many applications, the distance between the posts 30 will be between 5 mm and 40 mm, and more particularly generally equal about 20 mm. The shaft 32 of each post 30 has a diameter sufficient to perform its structural function, as described in more detail below, and depends upon the material chosen for the base 22 and posts 30. The illustrated posts 30 comprise a plastic or polymer material, with a diameter between 0.5 mm and 5 mm and particularly about 2 mm.

It is contemplated that the shaft 32 may be formed in any of a variety of elongated shapes in addition to the cylindrical shape shown in the illustrated embodiments, such as square, triangular and the like to suit a particular application. As described in greater detail below, the elongated shape of the shaft 32 preferably generally matches the shape of the holes 74 in the catheter fitting 14.

The shaft 32 has a securing portion which inhibits migration of the catheter 12 and catheter fitting 14. The securing portion may comprise one or more elements described below.

One element that the securing portion may comprise includes a protrusion that extends radially from the shaft 32. As shown in FIGS. 2a, 3a and 4a, the protrusion comprises an enlarged tip or head 34 at the end distal from the base 22. At least a portion of the circumference of the head 34 is larger than the circumference of the shaft 32, desirably having a maximum circumference of 1.1 to 3 times the circumference of the shaft 32. FIG. 2a shows the head 34 having a generally hemispherical shape with a smooth surface and a maximum circumference at an overhanging lower surface or underside 36. It will be understood, however, that the head 34 can take a variety of other shapes, with or without an underside 36, such as for example, solid or hollow conicals, arrowheads, barbs, spheres, mushroom heads, and other types of radially projecting structures. A relatively blunt end 37 of the head 34 is preferred to avoid snagging on materials such as a health care provider's latex gloves or sheets on the patient's bed.

As seen in FIGS. 2a, 3a and 4a, the underside 36 is generally planar. However, the underside 36 may be curved to form a recess 38 in which a portion of the catheter fitting 14 may be retained. The underside 36 may also have a surface which is roughened or which incorporates ridges or other snagging devices (not shown) to further assist in retaining the catheter fitting 14. However, the underside 36 may also be smooth, for less expensive fabrication costs.

Figure 3B:
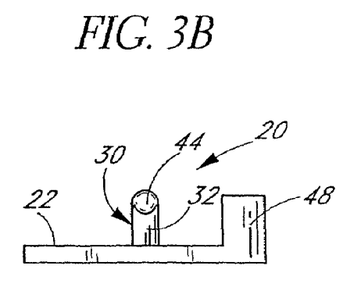
FIG. 3b is a front elevation view of the retainer of FIG. 2b.
Figure 4B:
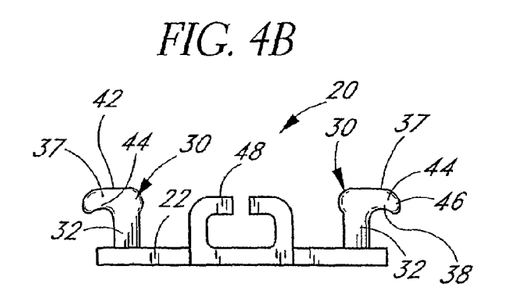
FIG. 4b is a side elevation view of the retainer of FIG. 3b.

Another element that the securing portion may comprise includes a hook 40. As shown in FIGS. 2*b*, 3*b* and 4*b*, the hook 40 has a radial portion 42 which extends outwardly from the shaft 32. Advantageously, the hook 40 has a curved portion 44 distal the shaft 32 and positioned toward a distal end of the radial portion 42 44. The curved portion 42 is sized and configured to accept a hole in the catheter fitting. Desirably, the curved portion 42 has a chamfer or taper 46 along the distal circumference to allow a medical attendant to easily fit the holes 74 in the catheter fitting 14 around the hook 40.

With reference now to FIGS. 1, 2*a* and 3*a* in general, the clip 48 is formed on the base 22. The illustrated embodiments show one clip 48 extending from the base 22. However, the base 22 can also include additional clips to suit a specific application, as noted above. For example, where the retainer 20 is designated to secure a relatively large catheter, the base can include two clips arranged on opposing ends of the catheter, for greater stability. Also, three clips can be used to firmly anchor a Y-site catheter.

The clip 48 is sized and shaped to readily accept a portion of the catheter 12 while not easily disengaging the accepted portion of the catheter 12. Advantageously, the clip 48 inhibits transverse movement of at least a portion of the catheter 12. Transverse movement of the catheter 12 is inhibited by contact with the clip 48, which is of sufficiently rigid construction and secured to the base 22 to act as a stop against advancement of the catheter 12 in the transverse direction. Inhibition of transverse movement of the catheter is advantageous because this movement can translate into movement of the catheter 12 at the engagement site between the catheter 12 (or catheter fitting 14) and post 30. This movement, in turn, can cause the catheter fitting 14 to roll or slip off the posts 30 and slide from engagement with the posts 30.

The clip 48 can be configured in a variety of ways to achieve its purpose. FIG. 2*a* illustrates a substantially C-shaped clip within which a portion of the catheter 12 is captured. FIG. 2*b* illustrates a pair of a semi-rigid, inverted L-shaped members that are closely spaced apart to releasably accept a catheter 12 that is sized greater than the spacing between the L-shaped members. As will be understood by one skilled in the art, a variety of other clip configurations, such as a single L-shaped clip, can be used to achieve the purpose of the clip.

The clip 48 may also include a hook portion 52 as described above, or a variety of other snagging, hooking and inhibiting devices as described above. The clip 48 can have a variety of sizes depending upon the particular application and the particular catheter 12 with which it is used.

In the illustrated embodiment, the clip 48 is arranged along a longitudinally extending line that substantially bisects a laterally extending line that extends between the two posts 30. An area 54 is formed on the retainer between the first and second sides and desirably laterally between the posts 30. The area 54 is sized and shaped so as to accept and retain a portion of a catheter 12 in a close fit manner between the posts 30 and the clip 48.

FIG. 1 illustrates an anchor pad 56 which desirably comprises a laminate structure with an upper foam layer (e.g., closed-cell polyethylene foam), and a lower adhesive layer. The lower adhesive layer constitutes the lower surface 58 of the anchor pad 56. The lower surface 58 desirably is a medical-grade adhesive and can be either diaphoretic or nondiaphoretic, depending upon the particular application. Such foam with an adhesive layer is available commercially from New Dimensions in Medicine of Columbus, Ohio. The illustrated embodiment shows the anchor pad 56 having suture holes 60 in addition to the adhesive layer to further secure the anchor pad 56 to the patient's skin. It will be understood, however, that the anchor pad 56 need not include suture holes 60 to secure the anchor pad 56 to the patient's skin.

A surface of the upper foam layer constitutes an upper surface 62 of the anchor pad 56. The upper surface 62 desirably is roughened by corona-treating the foam with a low electric charge. The roughened or porous upper surface 62 improves the quality of the adhesive joint (which is described below) between the base 22 and the anchor pad 56. In the alternative, the flexible anchor pad 56 can comprise a medical-grade adhesive lower layer, an inner foam layer and an upper paper or other woven or nonwoven cloth layer.

In the illustrated embodiment, the anchor pad 56 also desirably includes a pair of opposing crescent sections 64, 66 with a recess toward the proximal end 24 of the anchor pad 56 proximate to the clip 48. As a result, the lateral sides of the anchor pad 56 have more contact area which provides greater stability and adhesion to a patient's skin.

Figure 5:
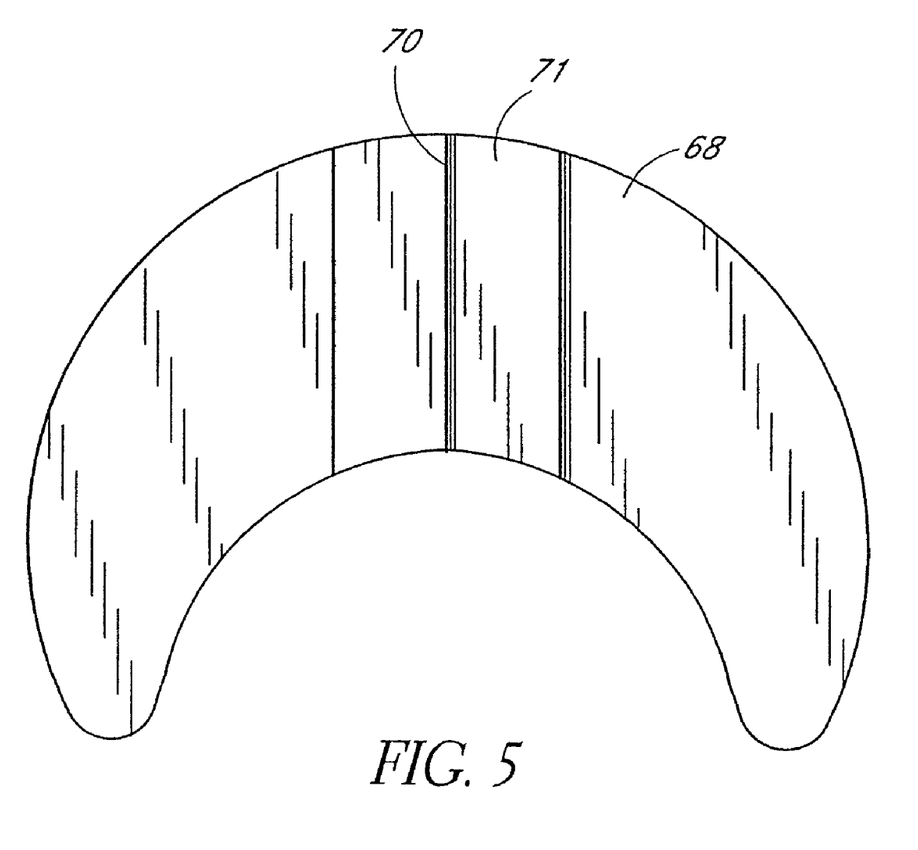
FIG. 5 is a bottom plan view of the anchor pad of FIG. 1.

FIG. 5 shows a removable paper or plastic release liner 68 which desirably covers the adhesive lower surface 58 before use. The liner 68 preferably resists tearing and desirably is divided into a plurality of pieces to ease attachment of the pad to a patient's skin. In the illustrated embodiment, the liner 68 is split along a center line 70 of the flexible anchor pad 56 in order to expose only half of the adhesive lower surface 58 at one time.

The liner 68 length extends beyond the center line 70 of the anchor pad 56 and is folded over, or back onto the liner 68. This folded over portion defines a pull tab 71 to facilitate removal of the liner 68 from the adhesive lower surface 58. A medical attendant uses the pull tab 71 by grasping and pulling on it so that the liner 68 is separated from the lower surface 58. The pull tab 71 overcomes any requirement that the medical attendant pick at a corner edge or other segment of the liner 68 in order to separate the liner 68 from the adhesive layer. The pull tab 71 of course can be designed in a variety of configurations. For example, the pull tab 71 need not be located along the center line 70 of the anchor pad 56; rather, the pull tab 71 may be located along any line or portion of the anchor pad 56 in order to ease the application of the anchor pad 56 onto the patient's skin at a specific site. For example, an area of a patient's skin with an abrupt bend, such as at a joint, may require that the pull tab 71 be aligned toward one of the lateral ends of the anchor pad 56 rather than along the center line 70.

The base 22 of the retainer 20 is attached to the upper surface 62 of the anchor pad 56. The base 22 desirably is secured to the upper surface 62 by a solvent bond adhesive, such as cyanoacrylate or other bonding material. One such adhesive is available commercially as Part No. 4693 from the Minnesota Mining and Manufacturing Company (3M).

When the anchoring system 10 is assembled as described above, the area 54 formed on the base 22 defines a receiving space 72. The receiving space 72 is capable of accepting a portion or length of the catheter 12. Although the receiving space 72 may take the form of various shapes depending upon its application (i.e., depending upon a shape of the retained portion of the medical article for which the retainer 20 is designed to be used), the receiving space 72 does have a sufficient length in the longitudinal direction to stabilize the catheter 12, rather than act as a fulcrum for the catheter 12, as mentioned above. That is, the longitudinal spacing between the posts 30 and the clip 48 on the retainer 20 is sized so as to receive sufficient length of the catheter 12 to inhibit movement of the catheter 12 in the lateral, longitudinal and transverse direction (i.e., to inhibit yaw, pitch and axial movement of the catheter 12), without kinking the catheter 12.

When the catheter fitting 14 is placed onto the posts 30 via the holes 74 and pressed onto the receiving space 72, a section of the catheter 12 is captured within the retainer 20. Desirably, the catheter fitting 14 is constructed of material that is more elastic than the retainer 20 and the distance between the posts 30 is slightly larger than the distance between the holes 74 in the catheter fitting 14. By this design, when the catheter fitting 14 is stretched to allow the posts 30 to accept the catheter fitting holes 74, a tensile force is applied to the catheter fitting 14 and a tight-fit relationship between the posts 30 and catheter fitting 14 exists to inhibit axial and rotational movement of the catheter 12. Rotational movement of the catheter 12 is further inhibited by the clip 30, as described above.

Figure 6:
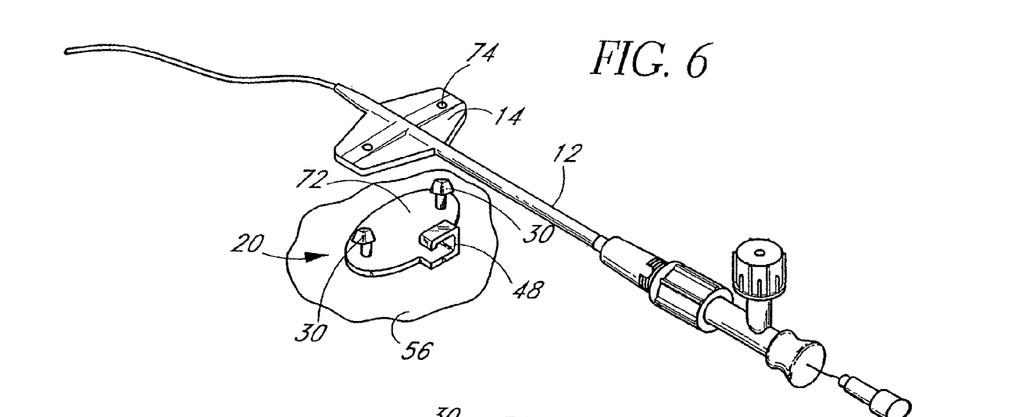
FIG. 6 is a top plan view of the anchoring system of FIG. 1 with a catheter fitting positioned above the retainer.
Figure 7:
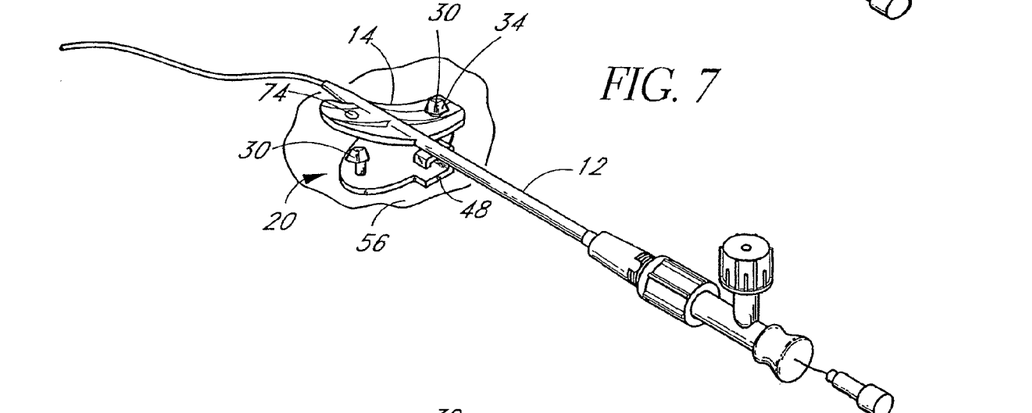
FIG. 7 is a perspective view of the anchoring system of FIG. 1 with the catheter fitting partially engaged with the retainer.
Figure 8:
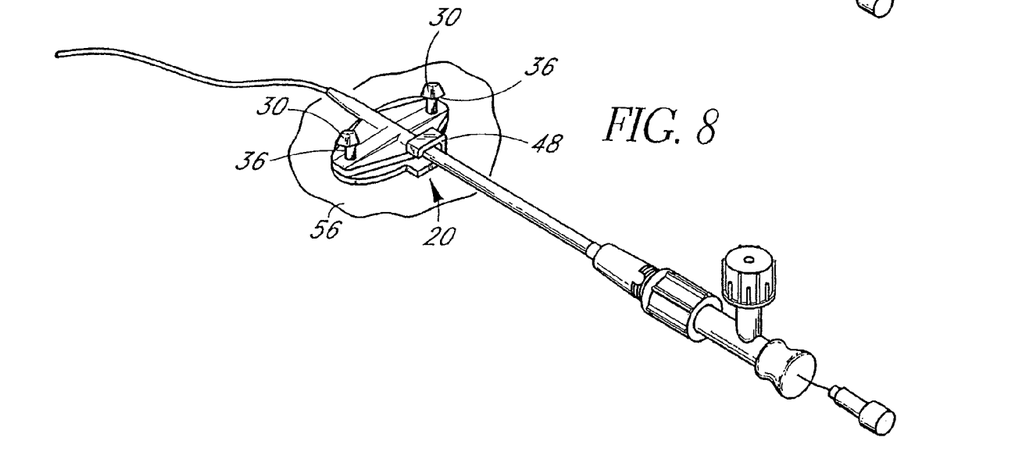
FIG. 8 is a perspective view of the anchoring system of FIG. 1 with the catheter fitting fully engaged with the retainer.

In operation and as illustrated in FIGS. 6-8, a medical attendant may secure a catheter 12 (or other medical article) to a patient using the above-described anchoring system (or a readily apparent modification thereof). The medical attendant first transversely aligns the holes 74 in the catheter fitting 14 over the posts 30. The catheter 12 may then be placed into the receiving space 72 formed between the lateral sides of the base 22 by engaging the holes 74 in the catheter fitting 14 around the post 30. This is done by first inserting a first post into one of the suture holes 74, as seen in FIG. 7, and then stretching the fitting 14 so as to align the other suture hole 74 over the second post 30. The fitting 14 is then slipped over the second post 30 by inserting the post 30 into the hole 74. In doing so, the catheter fitting 14 is hooked under the lower surface 36 of the post 30. The interaction between the under surface 36 and the portions of the catheter fitting 14 about the suture holes 74 inhibits the catheter fitting from pulling off the posts 30 in a transverse direction. And the general interaction between the posts 30 and the fitting 14 inhibits significant (i.e., meaningful) longitudinal and lateral movement of the catheter 12 relative to the retainer 20.

As seen in FIG. 8, a distal section of the catheter 12 is inserted into the clamp 48 by positioning the catheter 12 next to an opening in the clip 48 and pulling the catheter 12 into the clip. The deformable nature of the catheter 12, and/or the deflectable nature of the clip 48 permits the catheter section to be inserted into a space between at least a section of the clip 48 and the base 22. Importantly, a portion of the clip 48 extends generally parallel to the base 22 and generally normal to the posts 30. This section of the clip 48 prevents the distal portion of the catheter 12, which is unsecured behind clip 48, from applying a transverse force on the catheter fitting 14 when pulled transversely away from the retainer. As a result of this design, greater transverse force can be applied to the catheter before it disengages from the retainer, in comparison to a design that does not include a clip 48.

If the catheter 12 is pulled in an axial or rotational direction, interaction between the posts 30, clip 48 and catheter fitting 14 also prevents the catheter 12 from appreciable movement. The retainer 20 thus inhibits axial or rotational movement of the catheter 12 relative to the retainer 20.

Importantly, the posts 30 and clip 48 do not crimp or kink the catheter 12 body when it is inserted within the receiving space 72. Moreover, although the post 30 and clip 48 bear against the catheter, their limited pressure does not significantly occlude the corresponding catheter 12 lumen(s). Although FIG. 8 illustrates a space between the securing portions 34 of the posts 30 and the catheter fitting 14, the shafts 32 of the posts 30 can be sized for a particular catheter fitting 14 so as to reduce the amount of transverse play of the catheter fitting within the anchoring system when secured.

Figure 9:
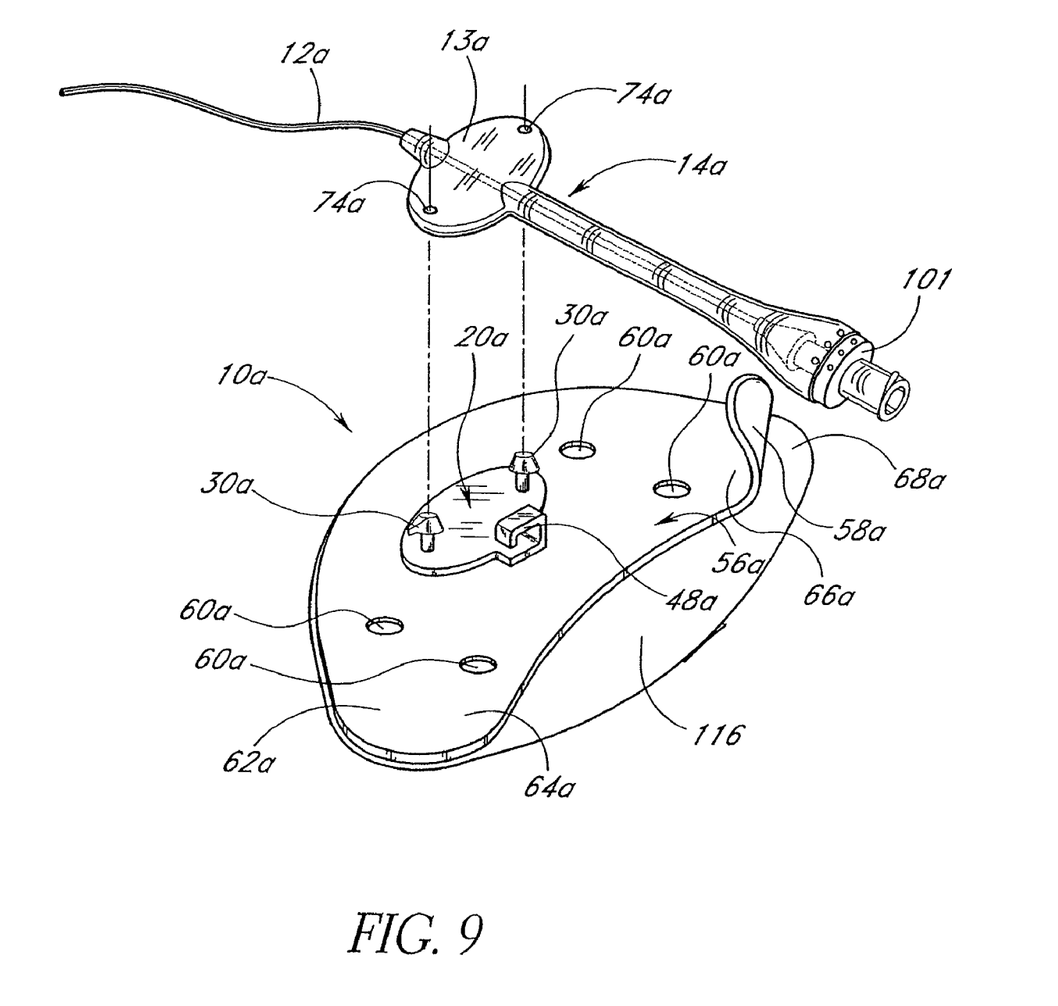
FIG. 9 is a perspective view of an anchoring system in accordance with another preferred embodiment of the present invention and illustrates an exemplary catheter positioned above the anchoring system.
Figure 10A:
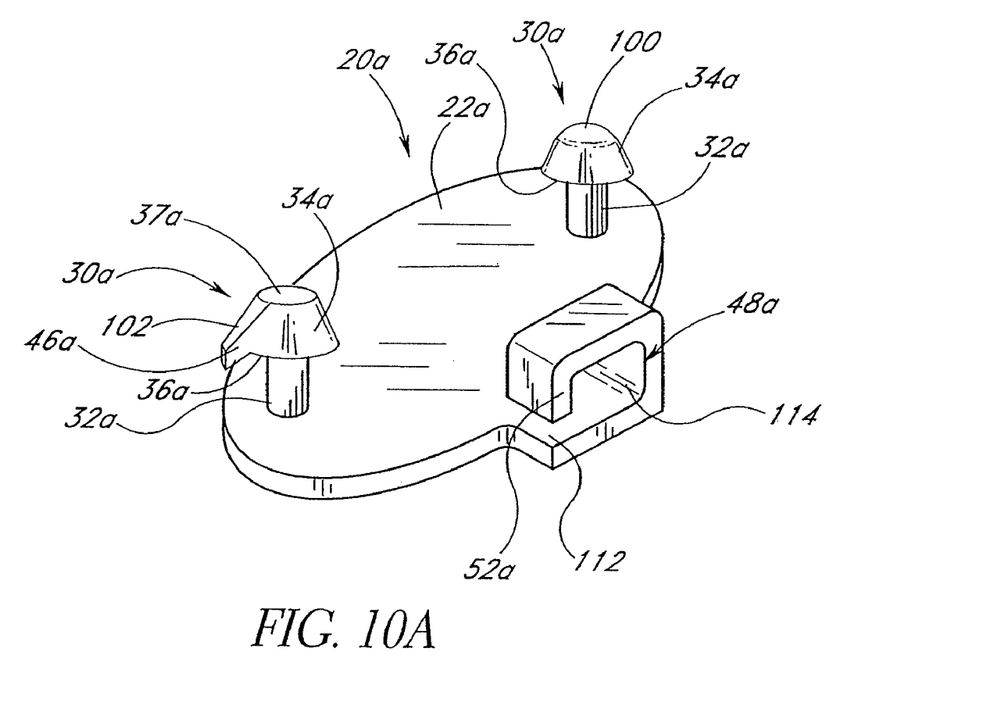
FIG. 10a is a perspective view of a retainer of the anchoring system of FIG. 9.
Figure 10B:
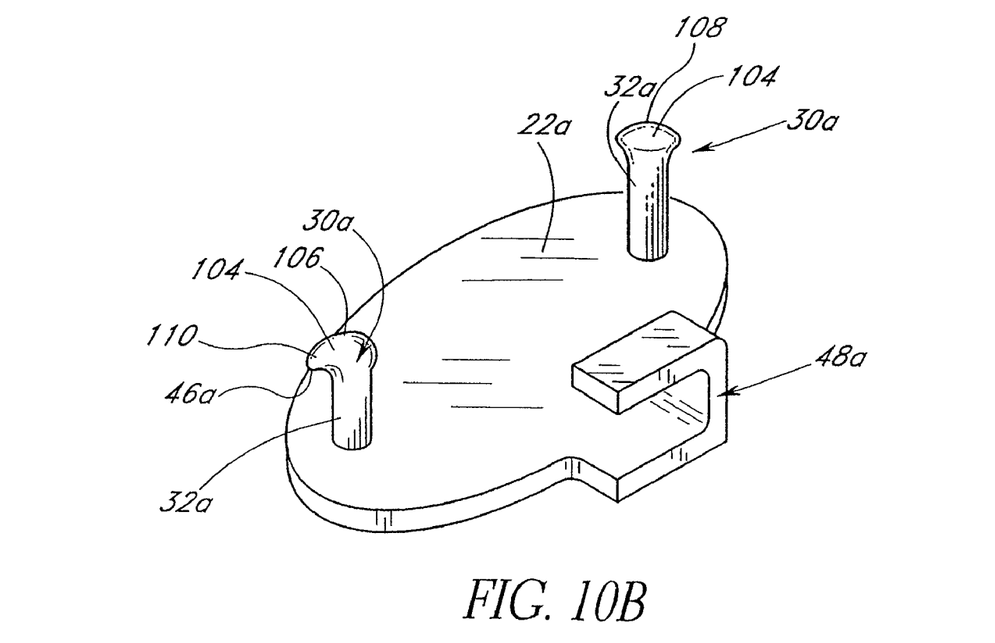
FIG. 10b is a perspective view of another embodiment of a retainer that can be used with an anchoring system similar to that of FIG. 9.

FIGS. 9 and 10 illustrate an anchoring system configured in accordance with another embodiment of the present invention. Like the anchoring system of the previous embodiment, this anchoring system includes a retainer with at least one retention member and an anchor pad. However, the particular configuration of these elements differs slightly. Also, the particular configuration of the medical article that connects to the anchoring system differs. Thus, for consistency, like numbers with an "a" suffix have been used to indicate like parts of the anchoring system of FIGS. 1-8. The above description of the like components thus should be understood as applying equally to the present embodiment of the anchoring system 10a, unless otherwise stated.

With reference to FIG. 9, the illustrated catheter fitting 14a is constructed entirely from a silicon material for pliability purposes, which allows the pair holes 74a in the laterally extending wing portion 13a of the fitting 14a to be enlarged during connection or disconnection operations. The catheter fitting 14a also has an elongate body with an inner lumen that houses the catheter 12a and can be attached to a plastic connecting piece 10. The exemplary midline catheter 12a is available commercially from Becton, Dickinson and Company of Sandy, Utah as First Mid-Cath™.

Like the previous embodiment, the retainer 20a is constructed, sized and configured to receive a portion of the catheter fitting 14a and to provide space on which to locate at least one retention member.

With reference to FIG. 10, the first retention member desirably comprises two laterally spaced posts 30a, although one, three or more posts can be used. Each post 30a includes a shank or shaft 32a attached to and extending generally upright from the base 22a. Each shaft 32a has a length of about 2 mm to 20 mm and desirably about 4 mm, and is laterally spaced apart a distance of 5 mm to 40 mm from the other shaft 32a, and desirably about 20 mm. The shaft 32a of each post 30a has a diameter sufficient to perform its structural function, with the illustrated shafts 32a having a diameter between 0.5 mm and 5 mm and desirably about 2 mm.

The shaft 32a may include a securing portion to inhibit migration of the catheter 12a and catheter fitting 14a relative to the shaft 32a. If used, the securing portion may comprise one or more elements previously described or described below. Alternatively, the shaft 32a may forgo use of a securing portion to assist in connecting or disconnecting operations, as explained below.

One element that the securing portion may comprise is a protrusion that extends radially outwardly from the end of the shaft 32a distal the base 22a. As best shown in FIG. 10A, the protrusion comprises a generally smooth angular enlarged tip or head 34a with an underside 36a that radially extends around the entire diameter of the shaft 32a. It will be understood, however, that the head 34a can take a variety of other shapes, with or without an underside 36a or portion thereof, such as for example, solid or hollow conicals, arrowheads, barbs, spheres, mushroom heads, hemispheres and other types of radially projecting structures. A relatively blunt end 37a of the head 34a is preferred to avoid snagging on materials such as a health care provider's latex gloves or sheets on the patient's bed. Alternatively, a relatively rounded end 100 of the head 34a is preferred to assist in fitting the holes 74a over the head 34a. At least one of the heads 34a may optionally include an angled extended portion 102 that faces away from the other post 30a. The angled portion 102 is sized and configured to accept the hole 74a of the catheter fitting 14a and desirably has a chamfer or taper 46a along the outer end to more easily fit the hole 74a of the catheter fitting 14a around the angled portion 102. Once the hole 74a is fitted around the angled portion 102, the hole 74a can be advanced/ stretched around the head 34a and then onto the shaft 32a.

Another element that the securing portion may comprise is also a protrusion that extends radially outwardly from the end of the shaft 32a distal the base 22a. As shown in FIG. 10B, the protrusion comprises a generally smooth rounded enlarged tip or bulb 104 not having an underside. However, an underside that radially extends around the entire length of the shaft 32a or a portion thereof could be used. A relatively blunt end 106 of the bulb 104 is preferred to avoid snagging on materials such as a health care provider's latex gloves or sheets on the patient's bed. Alternatively, a relatively rounded end 108 of the bulb 104 is preferred to assist in fitting the holes 74a around the bulb 104. The bulb 104 may optionally include a curved extended portion 110 that faces away from the other post 30a. The curved portion 110 is sized and configured to accept the hole 74a in the catheter fitting 14a and desirably has a chamfer or taper 46a along the free end to more easily fit the hole 74a in the catheter fitting 14a around the curved portion 110. Once the hole 74a is fitted around the curved portion 110, the hole 74a can be advanced around the bulb 104 and then onto the shaft 32a.

As noted above, both shafts 32a need not include a securing portion. If a securing portion is not used, the end of the shaft 32a distal the base 22a desirably has a smooth slightly rounded surface. This configuration assists in fitting the holes 74a in the catheter fitting 14a onto the shaft 32a. This configuration (not shown) provides for more easy engagement of the hole 74a with the shaft 32a (i.e. the hole 74a is not required to further enlarge to fit over the head 34a or bulb 104); however, the use of the securing portion 34a on both shafts 32a increases the security of the catheter fitting 14a on the retainer 20a.

With reference again to FIG. 10, the second securing member comprises a clip 48a that extends from the base 22a. Like the previous embodiment, the clip 48a is sized and shaped to readily accept a portion of the catheter fitting 14a or a section of the catheter 12a while not easily disengaging the accepted portion of the catheter fitting 14a or catheter 12a. Advantageously, the clip 48a also inhibits transverse movement of at least a portion of the catheter fitting 14a.

The clip 48a can be configured in a variety of ways to achieve its purpose. For example, FIG. 10A shows the clip 48a being generally C shaped and configured generally similar to the clip of FIG. 2A. However, the present embodiment of the clip 48a has a larger, more defined hook portion 52a that extends toward the base 22a to narrow or partially occlude the entranceway 112 into the clip interior 114. The narrowed entranceway 112 requires the medical attendant to flatten or otherwise contort a portion of the catheter fitting 14a when passing it through the entranceway 112 and into the clip interior 114. Once a portion of the catheter fitting 14a is positioned within the clip interior 114, the narrowed entranceway 112 requires that a portion of the catheter fitting 14a be flattened or otherwise contorted to dislodge the catheter fitting 14a from the clip interior 114. This arrangement inhibits accidental dislodgment of the catheter fitting 14a from the clip interior 114. In particular, the illustrated narrowed entranceway 112 has a transverse height that is less than three quarters of the transverse height of the catheter fitting 14a and desirably less than ½ the transverse height of the catheter 12a and more desirably about one-half of the transverse height of the catheter fitting 14a. Stated alternatively, for use in connection with the illustrated catheter fitting 14a, the narrowed entranceway 112 has a transverse height of about 1 mm to 5 mm and desirably about 3 mm.

For another example, FIG. 10B shows the clip 48a being a generally inversely L-shaped and configured generally similar to the clip of FIG. 2B. However, the present embodiment of the clip 48a does not include any hook portion at all. Thus, the entranceway 112 to the clip interior 114 is not narrowed or partially occluded, which facilitates insertion or removal of the catheter fitting 14a into the clip interior 114. In particular, the clip 48a has a transverse height than is the same or slightly greater than the transverse height of the catheter fitting 14a, or, for use with the illustrated catheter fitting 14a, about 3 to 10 mm and desirably about 6 mm.

FIG. 9 illustrates an anchor pad 56a including a laminate structure with an upper foam layer 62a, a lower adhesive layer 58a and suture holes 60a formed through the layers 58a, 62a that is constructed similar to the anchor pad of FIG. 1. Although the particular configuration of the anchor pad 56a is generally similar to the anchor pad of FIG. 1 (i.e. includes a pair of opposing crescent sections 64a, 66a with a recess area 116 toward the clip 48a end of the pad 56a), the particular configuration of the anchor pad 56a has a less severe pair of opposing crescent sections 64a, 66a and a less defined recess area 116. This configuration provides sufficient contact area for greater stability and adhesion to a patient's skin. Also, the anchor pad 56a is not sized and configured generally similar to the size and shape of the release liner 68a. That is, the release liner 68a covers the adhesive lower surface 58a of the anchor pad 56a as well as the recess area 116.

FIG. 10A illustrates a particularly advantageous embodiment of the anchoring system 10a. The anchoring system 10a utilizes a first retention member that comprises a pair of posts 30a wherein one post has a securing portion including a head 34a with a relatively blunt end 37a and a tapered angled extended portion 102, and the other post has a securing portion including a head 34a with a relatively rounded end 100 and no angled extended portion. This combination allows the medical attendant to easily connect the catheter fitting 14a to the retainer 20a by first fitting a hole 74a in the catheter fitting 14a through the angled extended portion 102 of the post 30a, then over the head 34a, and then onto the shaft 32a. The other hole 74a in the catheter fitting 14a can then be fit onto the other post 30a (which does not have the angled extended portion 102). The other hole 74a can be more easily fit onto the other shaft 32a via the rounded end 100 than if the other shaft 32a included a blunt end 37a or further included an angled extended portion 102 that faced away from the secured hole 74a. Thus, by this synergistic configuration, the holes 74a are easily fit onto both posts 30a and both posts 30a have a securing portion to inhibit catheter migration. The illustrated anchoring system also includes a second retention member embodied as a clip 48a with a hook portion 52a that transversely narrows the entranceway 112 to the clip interior 114 to about ½ the transverse height of the catheter 12a.

FIG. 10B illustrates another particularly advantageous embodiment of the anchoring system 10a that uses the combination of a first retention member comprising a pair of posts 30a wherein one post has a securing portion including a bulb 104 with a relatively blunt end 106 and an curved extended portion 110, and the other post 30a has a securing portion including a bulb 104 with a relatively rounded end 108 and no curved extended portion. Like the embodiment of FIG. 10A, this combination allows the medical attendant to easily connect the catheter 12a to the retainer 20a by first fitting a hole 74a in the catheter fitting 14a through the curved extended portion 110, then over the bulb 104, and then onto the shaft 32a. The other hole 74a in the catheter fitting 14a can then be fit onto the other post 30a (which does not have a curved extended portion 110). The other hole 74a can be more easily fit onto the other shaft 32a via the rounded end 108 than if the other shaft 32a included a blunt end 106 or further included a curved extended portion 110 that faced away from the secured hole 74a. Thus, by this synergistic configuration, the holes 74a are easily fit onto both posts 30a and both posts 30a have a securing portion to inhibit catheter migration. The illustrated anchoring system 10a also includes a second retention member embodied as a clip 48a without a hook portion 52a so that the transverse height of the entranceway 112 is not narrowed toward the clip interior 114.

The present anchoring system thus provides a sterile, tight-gripping, needle and tape-free way to anchor a catheter to a patient. The retainer 20 thus eliminates use of tape, and if prior protocol required suturing, it also eliminates accidental needle sticks, suture-wound-site infections and scarring. In addition, the retainer 20 can be configured to be used with any of a wide variety of catheters 12, fittings 14, tubes, wires, and other medical articles. Patient comfort is also enhanced and application time is decreased with the use of the present anchoring system.

Although this invention has been described in terms of certain preferred embodiments and suggested possible modifications thereto, other embodiments and modifications apparent to those of ordinary skill in the art are also within the scope of this invention. It is also understood that various aspects of one or several embodiments can be used with another or several embodiments. It is further understood that not all of the aspects or elements described in connection with a particular embodiment need to be utilized in connection with that or another embodiment. Accordingly, the scope of the invention is intended to be defined only by the claims which follow.

What is claimed is:

1. A securement system comprising:
    a medical article having a fitting that includes a pair of laterally extending wings; and
    a securement device comprising:
        a mounting layer having a mounting surface at least partially covered by an adhesive for attaching the securement device to the body of the patient;
        a base surface accessible from an opposite side of the mounting layer; and
        first and second retention surfaces each being distanced in a transverse direction from the base surface by a sufficient distance so as to define a receiving space therebetween, the receiving space being of a size so as to releasably accept at least a portion of the laterally extending wings, the first and second retention surfaces being arranged relative to each other so as to define an entranceway into the receiving space along a longitudinal axis, the entranceway having a lateral width less than a width of the fitting.

2. The securement device of claim 1 further comprising first and second inverted L-shaped clips, wherein the first retention surface is a first portion of a clip interior of the first inverted L-shaped clip and the second retention surface is a first portion of a clip interior of the second inverted L-shaped clip.

3. The securement device of claim 2, wherein the first inverted L-shaped clip interior comprises a second portion extending transversely toward the base surface and the second inverted L-shaped clip interior comprises a second portion extending transversely toward the base surface, and wherein a lateral distance between the second portion of the clip interior of the first L-shaped clip and the second portion of the clip interior of the second L-shaped clip is greater than the lateral width of the entranceway.

4. The securement device of claim 3, wherein the lateral distance between the second portions of the first and second inverted L-shaped clips is greater than a transverse height of the receiving space.

5. The securement device of claim 3, wherein the lateral distance between the second portions of the first and second inverted L-shaped clips is less than the width of a body of the medical article.

6. The securement device of claim 1, wherein the distance between the first and second retention surfaces and the base surface is less than a transverse height of at least a portion of the medical article so that movement of the retained portion of the medical article is inhibited by a holding effect provided by the first and second retention surfaces when said portion of the medical article is placed within the receiving space.

7. The securement device of claim 1, additionally comprising at least one post disposed on the base surface and extending in a transverse direction, the first post having a securing portion arranged toward an outer end of the first post.

8. The securement device of claim 7, wherein the post comprises a shaft, and wherein the securing portion includes a head, at least a portion of the head having a perimeter sized larger than a perimeter size of the shaft.

9. The securement device of claim 7, additionally comprising another post being disposed on the base surface and having a securing portion arranged toward an outer end of the said post.

10. The securement device of claim 9, further comprising first and second inverted L-shaped clips, wherein the first retention surface is a first portion of a clip interior of the first clip and the second retention surface is a first portion of a clip interior of the second clip, and wherein the receiving space between the two clips lies along a line that substantially bisects a line extending between the two posts.

11. The securement device of claim 10, wherein the base surface, posts, and clips are all parts of a unitary structure.

12. A securement system comprising:
    a medical article having an elongated body and a pair of laterally extending surfaces; and
    a securement device comprising:
        an anchor pad having a mounting surface at least partially covered by an adhesive layer for attaching the securement device to the patient's body, and a receiving surface oriented so as to face away from the patient's body, the receiving surface including a longitudinally extending section along which at least a portion of the medical article lies when secured by the securement device; and
        a pair of retention surfaces being spaced in a transverse direction from the receiving surface by a sufficient distance to releasably accept at least a portion of the laterally extending surfaces between the pair of retention surfaces and the receiving surface, inner edges of the pair of retention surfaces defining an entranceway along a longitudinal axis, the pair of retention surfaces and the receiving surface together defining a receiving space, the receiving space having a lateral dimension which is greater than a lateral dimension of the entranceway, wherein at least a portion of the laterally extending surfaces of the medical article is retained within the receiving space.

13. The securement device of claim 12, wherein the retention surfaces are interior portions of clip comprising two inverted L-shaped clip members.

14. The securement device of claim 13, wherein a clip interior of one of the two inverted L-shaped clips faces the clip interior of the other inverted L-shaped clip.

15. The securement device of claim 12, wherein a lateral distance between a second portion of the clip interior of one of the two inverted L-shaped clips and a second portion of the clip interior of the other inverted L-shaped clip is greater than the lateral width of the entranceway.

16. The securement device of claim 15, wherein the lateral distance is greater than a transverse height of the receiving space at least when the medical article is secured within the receiving space.

17. The securement device of claim 12, wherein the distance between the first and second retention surfaces and the base surface is less than a transverse height of a retained portion of the medical article at least when the retained portion is not secured within the receiving space so that movement of the retained portion is inhibited by a holding effect provided by the first and second retention surfaces when the retained portion is secured within the receiving space.

18. The securement device of claim 12, additionally comprising at least a first post extending from said receiving surface, the first post having a securing portion arranged toward an outer end of the first post.

19. The securement device of claim 18, wherein the retention surfaces are portions of two clips, and wherein the receiving surface, post, and clips are part of a unitary structure.

* * * * *

UNITED STATES PATENT AND TRADEMARK OFFICE
CERTIFICATE OF CORRECTION

| | | |
|---|---|---|
| PATENT NO. | : 7,520,870 B2 | Page 1 of 1 |
| APPLICATION NO. | : 11/266683 | |
| DATED | : April 21, 2009 | |
| INVENTOR(S) | : Steven F. Bierman | |

It is certified that error appears in the above-identified patent and that said Letters Patent is hereby corrected as shown below:

In Col. 7, Line 8, please delete "42 44" and insert --42--, therefor.

Signed and Sealed this

Twenty-sixth Day of January, 2010

David J. Kappos
*Director of the United States Patent and Trademark Office*